US007060765B2

(12) United States Patent
Vaughan et al.

(10) Patent No.: US 7,060,765 B2
(45) Date of Patent: Jun. 13, 2006

(54) LOW COMONOMER INCORPORATING METALLOCENE CATALYST COMPOUNDS

(75) Inventors: George Alan Vaughan, Houston, TX (US); Laughlin G. McCullough, League City, TX (US)

(73) Assignee: Univation Technologies, LLC, Houston, TX (US)

( * ) Notice: Subject to any disclaimer, the term of this patent is extended or adjusted under 35 U.S.C. 154(b) by 181 days.

(21) Appl. No.: 10/199,147

(22) Filed: Jul. 19, 2002

(65) Prior Publication Data

US 2004/0077785 A1 Apr. 22, 2004

Related U.S. Application Data

(60) Provisional application No. 60/306,503, filed on Jul. 19, 2001.

(51) Int. Cl.
*C08F 4/64* (2006.01)

(52) U.S. Cl. ............... 526/127; 526/160; 526/161; 526/172; 526/943

(58) Field of Classification Search ............... 526/127, 526/160, 161, 172, 170
See application file for complete search history.

(56) References Cited

U.S. PATENT DOCUMENTS

| 5,086,134 | A |   | 2/1992 | Antberg et al. |
| 5,359,015 | A |   | 10/1994 | Jejelowo ............... 526/114 |
| 5,382,630 | A |   | 1/1995 | Stehling et al. ............... 525/240 |
| 5,382,631 | A |   | 1/1995 | Stehling et al. ............... 525/240 |
| 5,679,812 | A |   | 10/1997 | Winter et al. ............... 556/7 |
| 5,786,495 | A |   | 7/1998 | Resconi et al. ............... 556/11 |
| 5,886,202 | A |   | 3/1999 | Jung et al. ............... 556/11 |
| 5,929,264 | A |   | 7/1999 | Rohrmann et al. ............... 556/11 |
| 5,990,253 | A | * | 11/1999 | van Beek et al. ............... 526/127 |
| 6,051,728 | A |   | 4/2000 | Resconi et al. ............... 556/53 |
| 6,087,290 | A | * | 7/2000 | Fottinger et al. ............... 502/103 |
| 6,111,019 | A |   | 8/2000 | Arjunan et al. ............... 525/211 |
| 6,214,469 | B1 |   | 4/2001 | Sukhadia et al. ............... 428/421 |
| 6,232,484 | B1 | * | 5/2001 | Schaverien et al. ............... 556/53 |

FOREIGN PATENT DOCUMENTS

| EP | 0 365 974 A3 | 5/1990 |
| EP | 0 365 974 A2 | 5/1990 |
| EP | 0 365 974 B1 | 12/1993 |
| EP | 0 664 301 A1 | 7/1995 |
| EP | 0693502 A1 | 1/1996 |
| EP | 0728773 A1 | 8/1996 |
| EP | 752428 A2 * | 1/1997 |
| EP | 0752428 A2 A3 | 1/1997 |
| EP | 0806436 A1 | 11/1997 |
| EP | 0 511 665 B1 | 7/1998 |
| EP | 0955304 A2 A3 | 11/1999 |
| EP | 1013675 A2 A3 | 6/2000 |
| WO | WO 94/11406 | 5/1994 |
| WO | WO 96/38458 | 12/1996 |
| WO | WO 98/28350 | 7/1998 |
| WO | WO 99/43724 | 9/1999 |
| WO | WO 00/31088 | 6/2000 |

OTHER PUBLICATIONS

Angew. Chem. 101 (1989) No. 11, 1536 Herrman, et al.
Hllger, W., et al., "*Erstes Belspiel eines ethylenselektiven löelichen Ziegler–Katalysators der Zirconocen–Klasse*", Angew. Chem. 101, No. 11, 1536–1538, (1989).
Koppl, A. et al: "*Homopolymerization of ethylene and copolymerization of ethylene and 1–hexene with bridged metallocene/methyllaluminoxane catalysts: the influence of the bridging moiety*" Journal of Molecular Catalysis A: Chemical, 153, 109–119 (2000).
Masahiro, Kishine et al: "*Ethylene copolymer injection moldings obtained by using metallocene catalysts*" retrieved from STN Database, abstract & JP 10 193379 A Mitsui Chemicals, Inc. Japan Jul. 28, 1998, abstract only.
Lehtinen, Christel et al: "*A comparison of $(\eta-butCp)_1ZrCl_1$ and other simple metallocenes with bridged $Et(Ind)2ZrCl_2$ and $Me_2Si(Ind)2ZrCl_2$ catalysts in tthene/propene copolymerization*" European Polymer Journal, 22(1). 115–120, (1997).
Galland, Griselda B. et al: "*13C–NMR study of ethylene/ 1–hexene and ethylene/1–octene copolymers obtained using homogeneous catalysts*" Polymer Bulletin 34 599–604, (1995).
He, Dawei et al: "*Metallocene polymerization catalyst for high molecular weight polyethylene and preparation thereof*" retrieved from STN Database, abstract & CN 1 149 060 A, Chemical Institute, Chinese Academy of Sciences, Peop. Rep. China, (May 7, 1997), abstract only.
Kawasaki, Masaaki et al: "*Ethylene copolymer rubbers prepared by using metallocene catalysts and crystalline polyolefin compositions containing them*" retrieved from STN Database, abstract & JP 09 012802 a Mitsui Petrochemical, IND Japan, Jan. 14, 1997, abstract only.
Hikuma, Shinji et al: "*New supports and manufacture thereof and polymerization catalysts for olefins*" retrieved from STN Database, abstract & JP 08 113604 a Show Denko KK, Japan May 7, 1996, abstract only.

(Continued)

Primary Examiner—Roberto Rabago
(74) Attorney, Agent, or Firm—Kevin M. Faulkner

(57) ABSTRACT

The present invention provides polymerization catalyst compounds, catalyst systems including these catalyst compounds, and to their use in the polymerization of ethylene and at least one comonomer. In particular, the invention relates to identifying the comonomer incorporation behavior of metallocene polymerization catalyst compounds. More particularly, the invention relates to identifying metallocene catalyst compounds which incorporate comonomer poorly. Preferably, such metallocene catalyst compounds contain at least one substituted or unsubstituted fused ring cyclopentadienyl based ligand. The invention also relates to the use of these low comonomer incorporating metallocene catalyst compounds in catalyst systems to produce polymers that are easy to process into a variety of articles, especially polyethylene based film, having enhanced properties.

25 Claims, 5 Drawing Sheets

OTHER PUBLICATIONS

Herfert, N. et al: "*Copolymerizatin of ethene and α–olefins with stereorigid metallocene/MAO Ziegler catalysts: kinetic and mechanistic insight*" Polymeric Materials Science and Engineering 97, 31–2, (1992).

Herfert N. et al: "*Elementarprozesse der Ziegler–katalyse, 6[13]) ethylen–und propenhomopolymerisation mit den stereorigiden katalysatorsystemen iPr[FluCp]ZrCl$_{2ZrC/ 2}$/MAO und Me$_2$Si[Ind]$_2$ZrCl$_1$/MAO$^b$)*" Macromol. Chem., vol. 193, No. 6, 1359–1367 (1992).

Imaeda, Kaori et al: "*.alpha.–Olefin polymerization catalyst components, catalysts, and preparation of .slphs.–olefin polymers with high yield, large molecular–weight, and narrow molecular–weight distribution*" retrieved from STN Database, abstract & JP 11 001508 A Mitsubishi Chemical Industries, Ltd. Japan Jan. 6, 1999.

Iwasaki, Takeshi et al: "*Olefin polymerization catalysts with high catalytic activity, and preparation of olefin–based polymers by using them*" retrieved from STN Database, abstract & JP 10 036423 a Idemitsu Kosan Co., Ltd., Japan, Feb. 10, 1998.

Kato, Taku et al: "*Synthesis of novel ansa–metallocene complex with bridged bis(indenyl) ligand and its application for olefin polymerization*" Science and Technology in Catalysis 473–476, p. 475 (1998).

Yao, Hui et al: "*Copolymerization of ethylene/1–octene with ansa–zirconocene catalysts*" retrieved from STN Database, abstract & Gaofenzi Xuebao (5), 612–615 (1998).

Jansen, Johannes Carolus et al: "*Evidence of the quasi–living character of the ansa–zirconocene/Mao– catalyzed copolymerization of ethylene and norbornene*" Macromol. Rapid Commun. 22(17), 1394–1398, (2001).

Schulze, U. et al: "*Structure and properties of ethene copolymers synthesized by metallocene catalysts*" J.M.S. Pure Appl. Chem. A35(7 & 8), 1037–1044, (1998).

Quijada, Raul et al: "*Study of the effect of the monomer pressure on the copolymerization of ethylene with 1–hexene*" Journal of Applied Polymer Science 64(13), 2567–2574, (1997).

Schaverien, Colin J. et al: "*A new class of chiral bridged metallocene: synthesis, structure, and olefin (Co) polymerization behavior of rac–and meso–1, 2–CH$_2$CH$_2${4–(7–Me–indenyl)}2SrCl$_2$*" Journal of the American Chemical Society 120(38), 9945–9946, (1998).

Mauler, Raquel S. et al: "*The effect of the ethylene pressure on its reaction with 1–hexene, 1–octene, and 4–methyl–1–pentene*" Polymer Bulletin 37(4), 469–474, (1996).

Alt, Helmut G. et al: "*Synthesis, characterization and polymerization potential of ansa–metallocene dichloride complexes of titanium, zirconium and hafnium containing a Si–N–Si bridging unit*" Journal of Organometallic Chemistry, 564(1–2), 109–114, (1998).

Xu, Guangxue et al: "*Copolymerization of ethylene with styrene using different constrained geometry catalysts*" Polymer Preprints 42(1), 474–475, (2001).

McKnight, Andrew L. et al: "*Ethylene/Norbornene copolymerizations with titanium CpA catalysts*" Macromolecules 32(9), 2816–2825, (1999).

Sernetz, Friedrich G. et al: "*Copolymerization of ethene with styrene using different methylaumoxane activated half–sandwich complexes*" Journal of Polymer Science, Part A: Polymer Chemistry 35(8), 1571–1578, (1997).

Xu, Guangxue et al: "*Copolymerization of 4–methyl–1–pentene and ethylene with new monocyclopentadienylamino titanium complexes*" Polymer Preprints 42(1), 470–471, (2001).

Schaverien, Colin J. et al: "*Ethylene Bis(2–indenyl) Ziroconocenes: A new class of diastereomeric metallocenes for the (Co)polymerization of α—olefins*" Organometallics 20(16), 3436–3452, (2001).

Forlini, Fabrizio et al: "[13] *C NMR study of the effect of coordinating solvents on zirconocene–catalyzed propene/1–hexene copolymerization*" Macromolecular Chemistry and Physics 203(4), 645–652, (2002).

Kaminsky, Walter et al: "*Tuning the ligand structure in metallocene polymerization catalysts*" Macromol. Symp. 183, 89–94, (2002).

\* cited by examiner

LOW COMONOMER INCORPORATING METALLOCENE CATALYST COMPOUNDS

This application claims the benefit of U.S. Provisional Application No. 60/306,503 filed Jul. 19, 2001. Such benefit is provided under 37 CFR § 1.78 (a)(3) and 35 USC § 120.

FIELD OF THE INVENTION

The present invention relates to polymerization catalyst compounds, catalyst systems including these catalyst compounds, and to their use in the polymerization of ethylene and at least one comonomer. In particular, the invention relates to identifying the comonomer incorporation behavior of metallocene polymerization catalyst compounds. More particularly, the invention relates to identifying metallocene catalyst compounds which incorporate comonomer poorly. Preferably, such metallocene catalyst compounds contain at least one substituted or unsubstituted fused ring cyclopentadienyl based ligand which is substantially directed to the front of the molecule, contains a long bridging group, or which contains a methyl substitution pattern which relates to poor comonomer incorporation. The invention also relates to the use of these low comonomer incorporating metallocene catalyst compounds in catalyst systems to produce polymers that are easy to process into a variety of articles, especially polyethylene based film, having enhanced properties.

BACKGROUND OF THE INVENTION

Metallocene catalyst compounds that are low comonomer incorporators typically show very low activity. In addition, polymer molecules of low comonomer content are, in general, relatively more crystalline and have a high melting temperature, which is disadvantageous in applications such as film where softness or clarity is desired. However, polymers produced by these low incorporators have been shown to be useful in preparing polymer blends. Such blends, for example, include two polymers with each polymer having the same molecular weight, but different comonomer content. Typically these blends have improved mechanical, physical and/or chemical properties and produce articles of manufacture with superior properties. For example, polymer blends prepared with broad bimodal composition distributions consisting of two narrow populations are known to have superior properties such as high tear values in films.

U.S. Pat. No. 5,382,630 to Stehling et al. discloses linear ethylene interpolymer blends made from components that can have the same molecular weight but different comonomer contents, or the same comonomer contents but different molecular weights, or comonomer contents that increase with molecular weight.

U.S. Pat. No. 6,051,728 to Resconi et al. discloses a class of metallocene compounds having two substituted cyclopentadienyl rings bridged by an alkylidene group wherein the groups can be indenyl groups. The metallocenes are characterized by (i) the cyclopentadienyl groups are substituted at the 3-position with a substituent other than hydrogen while the 2-position bears a hydrogen or is part of a condensed benzene ring; (ii) the bridge is a substituted-methylene bridge; and (iii) the cyclopentadienyl groups are identically substituted. These catalyst compositions are utilized in olefin polymerization and particularly in propylene polymerization. However, catalysts with short bridges, such as methylene bridges, particularly those with indenyl or flourenyl ligands, are generally known to have very high comonomer incorporation.

Angew. Chem. 101 (1989) No. 11, 1536 Herrman, Rohrmann et al. discusses four atom bridged bis-indenyl metallocenes.

There is a need in the industry for the ability to identify polymerization catalyst compounds having low comonomer incorporation and enhanced activity to produce polymers and polymer blends with enhanced properties.

In addition, there is a need in the industry for catalyst systems to produce polymers with enhanced properties imparted by low incorporator catalysts to produce polymers, utilizing more than one catalyst in a single reactor.

SUMMARY OF THE INVENTION

The present invention is directed to low comonomer incorporating metallocene catalyst compounds, which contain at least one fused ring cyclopentadienyl based ligand, and to their use in olefin(s) polymerization processes. The one or more fused ring cyclopentadienyl based ligand may be hydrogenated or substituted, and the ligand may be bridged or unbridged to another ligand. The invention is also directed to the use of these low comonomer incorporating catalyst compounds in catalyst systems for olefin(s) polymerization to produce polymers having enhanced properties that are easy to process, and especially to produce polymer films having enhanced properties. The preferred polymerization processes are gas phase or slurry phase processes, and are most preferably gas phase processes, especially where the catalyst system is supported.

In one embodiment, the invention provides for a polymerization process for the polymerizing of ethylene in combination with one or more other olefin(s) comonomers in the presence of a catalyst system comprising a low comonomer incorporating metallocene catalyst compound.

In another embodiment, the invention provides for a polymerization catalyst system including a low comonomer incorporating metallocene catalyst compound. In another embodiment, the invention provides for a method for identifying and selecting low comonomer incorporating metallocene catalyst compounds containing at least one fused ring cyclopentadienyl based ligand.

In another embodiment, the invention provides for a catalyst system including a low comonomer incorporator and at least one second catalyst compound. In another embodiment, the invention provides for use of such a catalyst system to prepare polymers in a single reactor.

In another embodiment the invention provides for a low comonomer incorporating metallocene having bridged or unbridged fused rings, which may be hydrogenated or substituted.

In another embodiment the invention provides for a low comonomer incorporating metallocene catalyst where the metallocene structure includes at least one fused ring cyclopentadienyl based ligand which is substantially directed to the front of the molecule, as defined herein.

In another embodiment the low comonomer incorporator of the invention is a bridged metallocene catalyst where the bridge contains more than 2 atoms.

In another embodiment, the invention provides for a low comonomer incorporating metallocene catalyst wherein the metallocene structure contains at least one substituted fused ring cyclopentadienyl based ligand wherein the selection and placement of the substituents affects the incorporation of comonomer.

In another embodiment the catalyst system of the invention includes substantially the rac isomer, both the rac and meso isomers, or substantially the meso isomer of the low comonomer incorporator.

DETAILED DESCRIPTION OF THE INVENTION

Introduction

Figure 1:
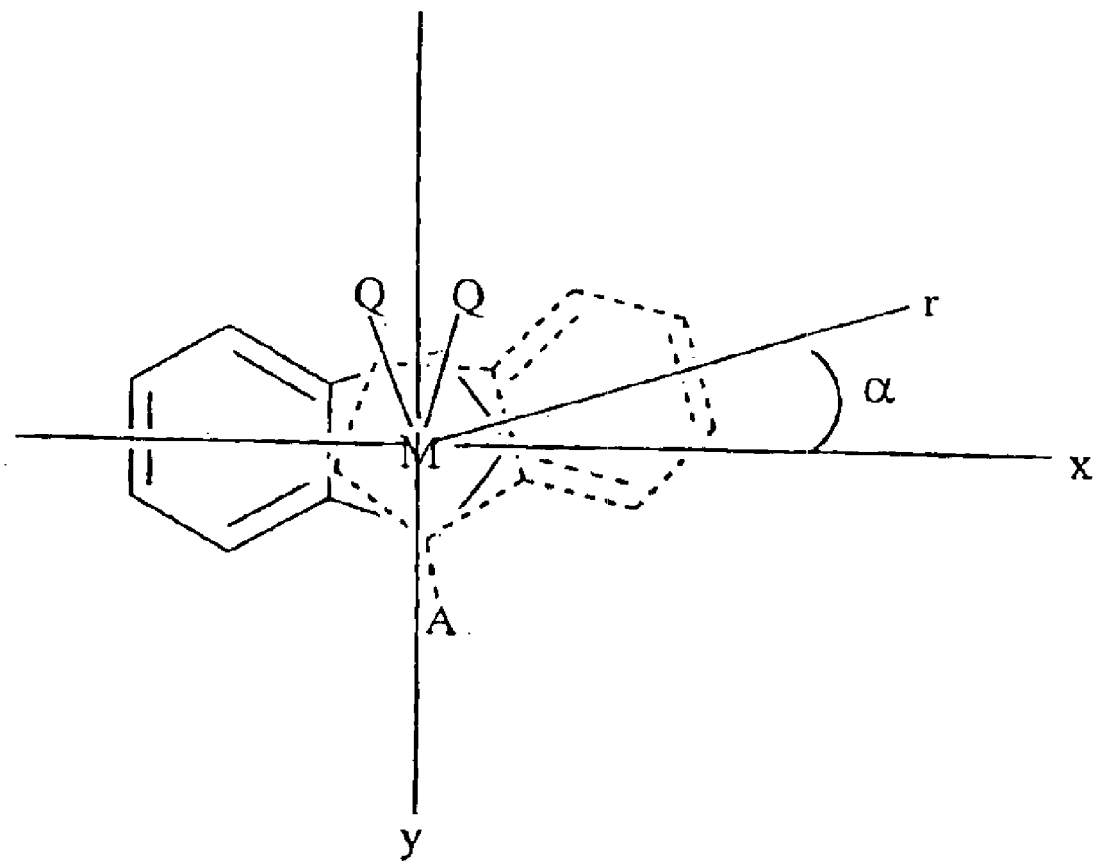
FIG. 1 is a top view of a metallocene showing an x axis placed over the metal atom M between leaving groups Q and bridging group A, a y axis placed over the metal atom M and bisecting leaving groups Q, and angle α defined by the bulky ligand centroids and the metal atom.

The present invention is directed to metallocene based polymerization catalyst compounds that contain at least one substituted or unsubstituted fused ring cyclopentadienyl based ligand, and which are poor comonomer incorporators, to identifying such poor comonomer incorporators, and their use in the polymerization of an olefin. Preferably, the catalysts of the invention are utilized in the polymerization of ethylene and at least one comonomer having from 3 to 10 carbon atoms.

For the purposes of this patent specification, the term "catalyst" refers to a metal compound, which when combined with an activator, polymerizes olefins. The term "activator" is used interchangeably with the term "co-catalyst", and the term "catalyst system" refers to the combination of a catalyst, an activator, and optionally a support material. The term "low incorporator" is defined further herein, and refers to a polymerization catalyst compound, preferably a metallocene polymerization catalyst compound, produces a higher density polyethylene, under similar processing parameters, when compared to bis (indenyl)zirconium dichloride.

Low Comonomer Incorporating Metallocene Catalyst Compound

The low comonomer incorporating metallocene catalyst compounds of the invention include half and full sandwich compounds having at least one, preferably, fused ring cyclopentadienyl based ligands, and at least one leaving group bonded to a metal atom. Fused ring cyclopentadienyl based ligands are those ligands including a substituted or unsubstituted cyclopentadienyl group which shares a pair of carbon atoms with another cyclic or aromatic structure.

The ring of the fused ring cyclopentadienyl based ligand is typically composed of atoms selected from Groups 13 to 16 atoms of the Periodic Table of Elements, preferably the atoms are selected from carbon, nitrogen, oxygen, silicon, sulfur, phosphorous, boron and aluminum or a combination thereof. Most preferably the ring of the fused ring cyclopentadienyl based ligand is composed of carbon atoms. Cyclopentadienyl based ligands also include other similar functioning ligand structures such as a pentadiene, a cyclooctatetraendiyl or an imide ligand.

The metal atom is preferably selected from Groups 3 through 15 and the lanthanide or actinide series of the Periodic Table of Elements. Preferably the metal is a transition metal from Groups 4 through 12, more preferably from Groups 4, 5 and 6, and most preferably the metal is from Group 4.

A "leaving group" for the purposes of this patent specification and appended claims is any ligand that can be abstracted from the metallocene catalyst compounds of the invention to form the metallocene catalyst cation capable of polymerizing one or more olefin(s).

In one embodiment, the low comonomer incorporating metallocene catalyst compound is represented by the Formula (I):

$$L^A(A)L^BMQ_n \qquad \text{Formula (I)}$$ 

where M is a Group 3 to 12 metal or an atom selected from the lanthanide or actinide series of the Periodic Table of Elements, preferably M is a Group 4, 5 or 6 transition metal, more preferably M is a Group 4 transition metal, more preferably M is zirconium, hafnium or titanium and most preferably M is zirconium.

$L^A$ and $L^B$ are independently bulky ligands, bonded to M, where preferably at least one of $L^A$ or $L^B$ is a fused ring cyclopentadienyl based bulky ligand. Bulky ligands are defined herein as open, acyclic, or fused ring(s) or ring system(s) such as unsubstituted or substituted, cyclopentadienyl ligands or cyclopentadienyl based ligands, heteroatom substituted and/or heteroatom containing ligands.

Non-limiting examples of bulky ligands include cyclopentadienyl ligands, indenyl ligands, benzindenyl ligands, fluorenyl ligands, octahydrofluorenyl ligands, cyclooctatetraendiyl ligands, azenyl ligands, azulene ligands, pentalene ligands, phosphoyl ligands, pyrrolyl ligands, pyrazolyl ligands, carbazolyl ligands, boratabenzene ligands and the like, including hydrogenated versions thereof, for example tetrahydroindenyl ligands.

Non-limiting examples of a fused ring cyclopentadienyl based ligand include indenyl ligands, benzindenyl ligands, fluorenyl ligands, octahydrofluorenyl ligands, cyclooctatetraendiyl ligands, azenyl ligands, azulene ligands, and the like, including hydrogenated versions thereof, for example tetrahydroindenyl ligands.

In one embodiment, $L^A$ and $L^B$ may be any other ligand structure capable of η-bonding to M, preferably $\eta^3$-bonding to M, and most preferably $\eta^5$-bonding to M wherein at least one of $L^A$ or $L^B$ is a fused ring cyclopentadienyl based ligand. In another embodiment, both $L^A$ and $L^B$ are fused ring cyclopentadienyl based ligands which may be the same or different.

In one embodiment, at least one of $L^A$ or $L^B$ and preferably both $L^A$ and $L^B$ are substituted or unsubstituted indenyl radicals.

In another embodiment, $L^A$ and $L^B$ may comprise one or more heteroatoms, for example, nitrogen, silicon, boron, germanium, sulfur and phosphorous, in combination with carbon atoms to form an open, acyclic, or preferably a fused, ring or ring system, for example, a hetero-cyclopentadienyl ancillary ligand. Other $L^A$ and $L^B$ bulky ligands include but are not limited to bulky amides, phosphides, alkoxides, aryloxides, imides, carbolides, borollides, porphyrins, phthalocyanines, corrins and other polyazamacrocycles.

Independently, each $L^A$ and $L^B$, as described above, may be unsubstituted or substituted with a combination of substituent groups R.

Non-limiting examples of substituent R groups include one or more from the group selected from hydrogen, linear or branched alkyl or alkenyl radicals, alkynyl radicals, cycloalkyl radicals, aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic alkylene radicals, or combination thereof.

Non-limiting examples of alkyl substituents R include methyl, ethyl, propyl, butyl, pentyl, hexyl, cyclopentyl, cyclohexyl, benzyl or phenyl groups and the like, including all their isomers, for example tertiary butyl, isopropyl, and the like. Other substituents R include hydrocarbyl radicals such as fluoromethyl, fluoroethyl, difluoroethyl, iodopropyl, bromohexyl, chlorobenzyl; hydrocarbyl substituted organometalloid radicals including trimethylsilyl, trimethylgermyl, methyldiethylsilyl and the like; halocarbyl-substituted organometalloid radicals including tris(trifluoromethyl)silyl, methyl-bis(difluoromethyl)silyl, bromomethyldimethylgermyl and the like; disubstitiuted boron radicals including dimethylboron for example; disubstituted pnictogen radicals including dimethylamine, dimethylphosphine, diphenylamine, methylphenylphosphine; and chalcogen radicals including methoxy, ethoxy, propoxy, phenoxy, methylsulfide and ethylsulfide.

Other substituents R include the atoms carbon, silicon, boron, aluminum, nitrogen, phosphorous, oxygen, tin, sulfur, germanium and the like. Substituent R groups also include olefins such as but not limited to olefinically unsaturated substituents including vinyl-terminated ligands, for example but-3-enyl, prop-2-enyl, hex-5-enyl and the like. Also, at least two R groups, preferably two adjacent R groups, may be joined to form a ring structure having from 3 to 30 atoms selected from carbon, nitrogen, oxygen, phosphorous, silicon, germanium, aluminum, boron or a combination thereof. Also, a substituent group R such as 1-butanyl may form a carbon sigma bond to the metal M.

Each Q is independently a leaving group bonded to M. In one embodiment, Q is a monoanionic labile ligand having a sigma-bond to M. Non-limiting examples of Q ligands include neutral weak bases such as amines, phosphines, dienes, andethers; monoanionic bases such as carboxylates, hydrocarbyl radicals having from 1 to 20 carbon atoms, hydrides or halogens and the like or a combination thereof. In another embodiment, two or more Q's form a part of a fused ring or ring system. Other examples of Q ligands include those substituents for R as described above and including cyclobutyl, cyclohexyl, heptyl, tolyl, trifluromethyl, tetramethylene, pentamethylene, methylidene, methoxy, ethoxy, propoxy, phenoxy, bis(N-methylanilide), dimethylamide, dimethylphosphide radicals and the like.

Depending on the oxidation state of the M, the value for n is 0, 1 or 2 such that formula (I) above represents a neutral metallocene catalyst compound.

A is an optional group. When A is present it is a bridging group bonded to $L^A$ and $L^B$. Non-limiting examples of bridging group A include groups containing at least one Group 13 to 16 atom(s), often referred to as a divalent moiety such as but not limited to at least one of a carbon, oxygen, nitrogen, silicon, aluminum, boron, germanium and tin atom or a combination thereof. Preferably bridging group A contains a carbon, silicon or germanium atom. More preferably bridging group A contains at least one, preferably 2 silicon atom(s) or at least one carbon atom. In another embodiment, A contains two or more, preferably more than two, preferably 3 to 4 and most preferably 3 Group 13 to 16 atoms.

In another embodiment, the bridging group A contains substituent groups R as defined above including halogens and iron. Bridging group A may be represented by R'$_2$C, R'$_2$Si, R'$_2$Si R'$_2$Si, R'$_2$Ge, R'P, R'$_2$Si—NR'—R'$_2$Si, or R'$_2$Si—O—R'$_2$Si where each R' is independently, a radical group which is hydride, hydrocarbyl, preferably alkyl having from 1 to 8 carbon atoms, substituted hydrocarbyl, halocarbyl, substituted halocarbyl, hydrocarbyl-substituted organometalloid, halocarbyl-substituted organometalloid, substituted boron, substituted pnictogen, substituted chalcogen, or halogen or two or more R' may be joined to form a ring or ring system. In another embodiment, the bridged metallocene catalyst compounds of Formula (I) may have two or more bridging groups A.

In another embodiment, the low comonomer incorporating metallocene catalyst compound is represented by Formula (II):

$$L^C AJMQ_n \qquad \text{Formula (II)}$$

where M is a Group 3 to 16 metal atom or a metal selected from the Group of actinides and lanthanides of the Periodic Table of the Elements, preferably M is a Group 4 to 12 transition metal, and more preferably M is a Group 4, 5 or 6 transition metal, and most preferably M is a Group 4 transition metal in any oxidation state. Most preferably M is zirconium or hafnium.

$L^C$ is bonded to M and is a fused ring cyclopentadienyl based bulky ligand as defined above, which may be substituted or unsubstituted by R as defined above.

J is a heteroatom ancillary ligand bonded to M. J contains an element with a coordination number of three from Group 15 or an element with a coordination number of two from Group 16 of the Periodic Table of the Elements. Preferably J contains a nitrogen, phosphorus, oxygen or sulfur atom with nitrogen being most preferred.

A is defined as above and is a bridging group bonded to $L^C$ and J.

Q is a univalent anionic ligand; and n is the integer 0,1 or 2.

In Formula (II) above, $L^C$, A and J form a fused ring system. In an embodiment, $L^C$ of Formula (II) is as defined as $L^A$ above. In another embodiment, A, M and Q of Formula (II) are as defined above in Formula (I).

In another embodiment the invention provides for a low comonomer incorporating metallocene catalyst where the metallocene structure includes at least one fused ring cyclopentadienyl based ligand, preferably two, which are substantially directed to the front of the molecule as defined below. The ligands may be directed to the front of the molecule by bridging group A or by substituent group(s). Referring to FIG. 1, which is a top view of one embodiment of a low comonomer incorporating metallocene of the present invention where metal M is in the plane of the page, a first ligand, here indenyl ligands, are present above (dashed lines) and below (solid lines) the plane of the page. The y axis passes through the metal atom M, lies in the plane of the page, and bisects leaving groups Q. The x axis passes through the metal atom M, lies in the plane of the page and intersects the y axis at a 90° angle. The front of the molecule is defined as towards leaving groups Q. Although bridging group A is present in FIG. 1, it is understood that bridging group A is optional and may or may not present. The ligands, which are represented by indenyl groups in FIG. 1, are directed to the front of the molecule at angle α. Angle α is defined as the angle between the x axis and r where r is the projection into the plane of the page of a line drawn between the centroid of the ring bonded to the metal, here a cyclopentadienyl ring, and the centroid of the fused ring, here a benzyl ring bonded to the cyclopentadienyl ring.

It is understood that if there are two fused cyclopentadienyl based ligands, referring again to FIG. 1, the angle α for the fused ring above the plane of the page may or may not be the same angle α for the fused ring below the plane of the page.

Angle α may be determined from X-ray crystallography and/or calculated from molecular modeling techniques, as is known in the art. In one embodiment, still referring to FIG. 1, α is greater than 30°, preferably greater than 45°, preferably greater than 60°, preferably between 30° and less than 90° and more preferably about 80° to about 90°.

In another embodiment two fused ring cyclopentadienyl based ligands are present and are bridged by at least 3 atoms selected from Groups 13 to 16 of the Periodic Table of the Elements, wherein the angle α of the first ligand is about 70° to about 90° preferably about 80° to about 90° and wherein angle α of the second ligand is greater than about 15°, preferably greater than about 30° and more preferably greater than about 45°.

In another embodiment the invention provides for a low comonomer incorporating metallocene catalyst where the metallocene structure includes at least one fused ring cyclopentadienyl based ligand bridged to another cyclopentadienyl ligand, as shown above in Formula I, where the bridge A is a long bridge defined as a bridge containing 2 or more, preferably 3 or more atoms. Preferably, a long bridge A includes oxygen silicon and carbon atoms, more preferably, long bridge A includes an Si—O—Si group where the silicon is substituted with an R group as defined above, preferably where R an alkyl or a nitrogen containing group. Long bridge A may also include Si—N—Si where the nitrogen and the silicon atoms are substituted, preferably with R groups as defined above, more preferably where R is an alkyl. Non-limiting examples of a suitable long bridged low incorporating metallocenes include $O(Me_2SiInd)_2ZrCl_2$, $O(Me_2SiFluorenyl)_2ZrCl_2$ $O(Me_2SiInd)_2HfCl_2$ $O(Me_2Si[Me_3Cp])_2ZrCl_2$, $O(Ph_2SiInd)_2ZrCl_2$, $RN(Me_2SiInd)_2ZrCl_2$, and $O(Me_2Si[Me_3Cp])(Me_2SiInd)ZrCl_2$. Preferably, these low incorporators are present in the rac or meso forms or a combination thereof. More preferably they are present as substantially the meso isomer. While not wishing to be limited by theory, the inventors believe that X-ray crystal structures show that long bridges swing around toward the front of the metallocene creating steric hinderance, and that in the case of meso-$O(Me_2SiInd)_2ZrCl_2$, for example, both of the indenyl rings are pointed to the front of the molecule making it further crowded. These steric features therefore, should disfavor approach of bulky alpha-olefins, such as alpha-olefins having 3 or more carbon atoms, preferably >3, >4, and more preferably >5 carbon atoms, to the metal center reducing their incorporation.

Referring again to FIG. 1, the long bridging group A provides for low comonomer incorporating metallocene. In one embodiment two fused ring cyclopentadienyl based ligand are present and are bridged by at least 3 atoms selected from Groups 13 to 16 of the Periodic Table of the Elements, wherein the angle α of the first ligand is about 80 to about 90° and wherein angle α of the second ligand is negative.

In one embodiment, for purposes of the present application, a low comonomer incorporator is defined herein as a polymerization catalyst which produces a higher density polyethylene than bis indenyl zirconium dichloride $(Ind)_2ZrCl_2$ when run under similar process conditions. For example, referring to FIG. 2 and Table 1, $(Ind)_2ZrCl_2$, produces a 0.920 density polyethylene at a hexene/ethylene ratio of 0.019. By comparison, (pentamethylcyclopentadienyl) (indenyl) zirconium dichloride requires a hexene/ethylene ratio of 0.036 to produce a 0.920 density polyethylene and is therefore defined herein as a low comonomer incorporator. Conversely, dimethylsilylene bis(4,5,6,7-tetrahydroindenyl)zirconium dichloride requires a hexane/ethylene ratio of 0.007 to produce a 0.917 density polyethylene and is therefore defined herein as a good incorporator.

In another embodiment, a low incorporator is defined herein as a polymerization catalyst, that when run under process conditions wherein $(Ind)_2ZrCl_2$ would produce a 0.920 density polyethylene, produces a polymer with a density greater than 0.920, preferably greater than 0.930, more preferably greater than 0.935, more preferably greater than 0.940, more preferably greater than 0.945 and even more preferably greater than 0.950.

In another embodiment the invention provides for a low comonomer incorporating metallocene catalyst where the metallocene structure includes at least one, preferably two fused ring cyclopentadienyl based ligand, preferably an indenyl based ligand, and most preferably contains two indenyl based ligand substituted to control comonomer incorporation. It has been determined that 1-substituted bisindenylzirconium dichloride compounds are much poorer comonomer incorporators in ethylene polymerization reactions compared to 2-substituted bisindenylzirconium dichloride compounds and other unbridged metallocenes. While substituents in the 4, 5, 6 and 7 position may affect activity, it has been determined that substituents present in the 1 position affect comonomer incorporation. Suitable substitutions in the 1-position which provide for low comonomer incorporation include alkyl groups such as methyl, ethyl and propyl groups.

For example, bis(1-methylindenyl)zirconium dichloride, $(1\text{-MeInd})_2ZrCl_2$, supported on silica (Davison 948, 0.35 wt % Zr, 120:1 moles MAO: moles $(1\text{-MeInd})_2ZrCl_2$) typically requires a hexene to ethylene ratio of 0.044 in the gas phase to make a 1.62 MI, 0.9195 g/cc polymer in a gas phase reactor. Similarly, bis(1-propylindenyl)zirconium dichloride, $(1\text{-PrInd})_2ZrCl_2$ typically requires a hexene to ethylene ratio of 0.039 to make a 1.68 MI, 0.9242 g/cc polymer. In contrast, bis(2-methylindenyl)zirconium dichloride, $(2\text{-MeInd})_2ZrCl_2$, only typically requires a hexene to ethylene ratio of 0.015 to make 0.47 MI, 0.9247 g/cc polymer. Bis(2-propylindenyl)zirconium dichloride, $(2\text{-PrInd})_2ZrCl_2$, also only typically requires a hexene to ethylene ratio of 0.014 to make a 4.65 MI, 0.9275 g/cc polymer.

Bis(propylcyclopentadienyl)zirconium dichloride, $(PrCp)_2ZrCl_2$, also only typically requires a hexene to ethylene ratio of 0.016 to make a 4.38 MI, 0.914 g/cc polymer, and bis(1,3-methylbutylcyclopentadienyl)zirconium dichloride, $(1,3\text{-MeBuCp})_2ZrCl_2$, also only typically requires a hexene to ethylene ratio of 0.014 to make a 1.06 MI, 0.9173 g/cc polymer.

Activators and Activation

The low comonomer incorporating metallocene polymerization catalyst compounds, described above, are typically activated in various ways to yield compounds having a vacant coordination site that will coordinate, insert, and polymerize olefin(s). For the purposes of this patent specification and appended claims, the term "activator" is defined to be any compound which can activate any one of the catalyst compounds described above by converting the neutral catalyst compound to a catalytically active catalyst compound cation. Non-limiting activators, for example, include alumoxanes, aluminum alkyls and ionizing activators, which may be neutral or ionic.

In one embodiment, alumoxanes activators are utilized as an activator in the catalyst composition of the invention. Alumoxanes are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage.

Aluminum alkyl or organoaluminum compounds which may be utilized as activators include trimethylaluminum, triethylaluminum, triisobutylaluminum, tri-n-hexylaluminum, tri-n-octylaluminum and the like.

It is also within the scope of this invention to use an ionizing or stoichiometric activator, neutral or ionic, such as tri(n-butyl)ammonium tetrakis (pentafluorophenyl)boron, a trisperfluorophenyl boron metalloid precursor or a trisperfluoronapthyl boron metalloid precursor, polyhalogenated heteroborane anions (WO 98/43983), boric acid (U.S. Pat. No. 5,942,459 incorporated herein by reference) or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, napthyl or mixtures thereof. Even more preferably, the three groups are halogenated, preferably fluorinated, aryl groups. Most preferably, the neutral stoichiometric activator is trisperfluorophenyl boron or trisperfluoronapthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124, all of which are herein fully incorporated by reference.

In a preferred embodiment, the stoichiometric activators include a cation and an anion component, and may be represented by the following formula:

$$(L-H)_d^+ (A^{d-}) \quad (X)$$

wherein L is an neutral Lewis base;
H is hydrogen;
$(L-H)^+$ is a Bronsted acid
$A^{d-}$ is a non-coordinating anion having the charge d–
d is an integer from 1 to 3.

The cation component, $(L-H)_d^+$ may include Bronsted acids such as protons or protonated Lewis bases or reducible Lewis acids capable of protonating or abstracting a moiety, such as an akyl or aryl, from the bulky ligand metallocene or Group 15 containing transition metal catalyst precursor, resulting in a cationic transition metal species.

The activating cation $(L-H)_d^+$ may be a Bronsted acid, capable of donating a proton to the transition metal catalytic precursor resulting in a transition metal cation, including ammoniums, oxoniums, phosphoniums, silyliums and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether diethyl ether, tetrahydrofuran and dioxane, sulfoniums from thioethers, such as diethyl thioethers and tetrahydrothiophene and mixtures thereof. The activating cation $(L-H)_d^+$ may also be an abstracting moiety such as silver, carboniums, tropylium, carbeniums, ferroceniums and mixtures, preferably carboniums and ferroceniums. Most preferably $(L-H)_d^+$ is triphenyl carbonium.

The anion component $A^{d-}$ include those having the formula $[M^{k+}Q_n]^{d-}$ wherein k is an integer from 1 to 3; n is an integer from 2–6; n–k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

In one embodiment, the ionic stoichiometric activator $(L-H)_d^+ (A^{d-})$ is N,N-dimethylanilinium tetra (perfluorophenyl)borate or triphenylcarbenium tetra (perfluorophenyl)borate.

In one embodiment, an activation method using ionizing ionic compounds not containing an active proton but capable of producing a bulky ligand metallocene catalyst cation and their non-coordinating anion are also contemplated, and are described in EP-A-0 426 637, EP-A-0 573 403 and U.S. Pat. No. 5,387,568, which are all herein incorporated by reference.

Method for Supporting

The above low comonomer incorporating metallocene catalyst compounds may be combined with one or more support materials or carriers using one of the support methods well known in the art or as described below. In the preferred embodiment, the method of the invention uses a polymerization catalyst in a supported form, for example deposited on, bonded to, contacted with, or incorporated within, adsorbed or absorbed in, or on, a support or carrier.

The terms "support" or "carrier" are used interchangeably and are any support material, preferably a porous support material, for example, talc, inorganic oxides and inorganic chlorides. Other carriers include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred carriers are inorganic oxides that include those Group 2, 3, 4, 5, 13 or 14 metal oxides. The preferred supports include silica, alumina, silica-alumina, magnesium chloride, and mixtures thereof. Other useful supports include magnesia, titania, zirconia, montmorillonite, zeolites, and the like. Also, combinations of these support materials may be used, for example, silica-chromium, silica-alumina, silica-titania and the like.

It is preferred that the carrier, most preferably an inorganic oxide, has a surface area in the range of from about 10 to about 700 $m^2/g$, pore volume in the range of from about 0.1 to about 4.0 cc/g and average particle size in the range of from about 5 to about 500 μm. More preferably, the surface area of the carrier is in the range of from about 50 to about 500 $m^2/g$, pore volume of from about 0.5 to about 3.5 cc/g and average particle size of from about 10 to about 200 μm. Most preferably the surface area of the carrier is in the range is from about 100 to about 400 $m^2/g$, pore volume from about 0.8 to about 3.0 cc/g and average particle size is from about 5 to about 100 μm. The average pore size of the carrier of the invention typically has pore size in the range of from 10 to 1000 Å, preferably 50 to about 500 Å, and most preferably 75 to about 350 Å.

Examples of supporting the metallocene catalyst systems of the invention are described in U.S. Pat. Nos. 4,701,432, 4,808,561, 4,912,075, 4,925,821, 4,937,217, 5,008,228, 5,238,892, 5,240,894, 5,332,706, 5,346,925, 5,422,325, 5,466,649, 5,466,766, 5,468,702, 5,529,965, 5,554,704, 5,629,253, 5,639,835, 5,625,015, 5,643,847, 5,665,665, 5,698,487, 5,714,424, 5,723,400, 5,723,402, 5,731,261, 5,759,940, 5,767,032 and 5,770,664 and U.S. application Ser. No. 271,598 filed Jul. 7, 1994 and Ser. No. 788,736 filed Jan. 23, 1997 now U.S. Pat. Nos. 5,468,702 and 6,090,740, respectively, and PCT publications WO 95/32995, WO 95/14044, WO 96/06187 and WO 97/02297 all of which are herein fully incorporated by reference.

In one embodiment, the low comonomer incorporating metallocene catalyst compounds of the invention may be deposited on the same or separate supports together with an activator, or the activator may be used in an unsupported form, or may be deposited on a support different from the supported metallocene catalyst compounds of the invention, or any combination thereof.

Procedures for measuring the total pore volume of a porous support are well known in the art. Details of one of these procedures is discussed in Volume 1, *Experimental Methods in Catalytic Research* (Academic Press, 1968) (specifically see pages 67–96). This preferred procedure involves the use of a classical BET apparatus for nitrogen absorption. Another method well known in the art is described in Innes, *Total Porosity and Particle Density of Fluid Catalysts By Liquid Titration*, Vol. 28, No. 3, Analytical Chemistry 332–334 (March, 1956).

The mole ratio of the metal or metalloid of the activator component to the metal of the supported metallocene catalyst compound or catalyst compounds is in the range of between 0.3:1 to 1000:1, preferably 20:1 to 800:1, and most preferably 50:1 to 500:1. Where the activator is an ionizing activator such as those based on the anion tetrakis (pentafluorophenyl)boron, the mole ratio of the metal or metalloid of the activator component to the metal component of the metallocene catalyst is preferably in the range of between 0.3:1 to 3:1.

Where an unsupported metallocene catalyst system is utilized, the mole ratio of the metal or metalloid of the activator component to the metal of the metallocene catalyst compound is in the range of between 0.3:1 to 10,000:1, preferably 100:1 to 5000:1, and most preferably 500:1 to 2000:1.

In one embodiment the low comonomer incorporating polymerization catalyst is used in an unsupported form, preferably in a liquid form such as described in U.S. Pat. Nos. 5,317,036 and 5,693,727 and European publication EP-A-0 593 083, all of which are herein incorporated by reference. The polymerization catalyst in liquid form can be fed to a reactor as described in PCT publication WO 97/46599, which is fully incorporated herein by reference.

In one embodiment of the invention, olefin(s), preferably $C_2$ to $C_{30}$ olefin(s) or alpha-olefin(s), preferably ethylene or propylene or combinations thereof are prepolymerized in the presence of the low comonomer incorporating metallocene catalyst system of the invention prior to the main polymerization. The prepolymerization can be carried out batchwise or continuously in gas, solution or slurry phase including at elevated pressures. The prepolymerization can take place with any olefin monomer or combination and/or in the presence of any molecular weight controlling agent such as hydrogen. For examples of prepolymerization procedures, see U.S. Pat. Nos. 4,748,221, 4,789,359, 4,923,833, 4,921,825, 5,283,278 and 5,705,578 and European publication EP-B-0279 863 and PCT Publication WO 97/44371 all of which are herein fully incorporated by reference.

In one embodiment, the low comonomer incorporating polymerization catalysts of the invention can be combined with a carboxylic acid salt of a metal ester, for example aluminum carboxylates such as aluminum mono, di- and tri-stearates, aluminum octoates, oleates and cyclohexylbutyrates, as described in U.S. application Ser. No. 09/113,216, filed Jul. 10, 1998, now abandoned.

Polymerization Process

The catalysts and catalyst systems of the invention described above are suitable for use in any polymerization process over a wide range of temperatures and pressures. The temperatures may be in the range of from −60° C. to about 280° C., preferably from 50° C. to about 200° C. In one embodiment, the polymerization process is conducted above 70° C. and preferably above 80° C. The pressures employed may be in the range from 1 atmosphere to about 500 atmospheres or higher.

Polymerization processes include solution, gas phase, slurry phase and a high pressure process or a combination thereof. Particularly preferred are a gas phase or slurry phase polymerization process of one or more olefins at least one of which is ethylene.

In one embodiment, the process of this invention is directed toward a solution, high pressure, slurry or gas phase polymerization process of one or more olefin monomers having from 2 to 30 carbon atoms, preferably 2 to 12 carbon atoms, and more preferably 2 to 8 carbon atoms. The invention is particularly well suited to the polymerization of two or more olefin monomers of ethylene, propylene, butene-1, pentene-1, 4-methyl-pentene-1, hexene-1, octene-1 and decene-1.

Other monomers useful in the process of the invention include ethylenically unsaturated monomers, diolefins having 4 to 18 carbon atoms, conjugated or nonconjugated dienes, polyenes, vinyl monomers and cyclic olefins. Non-limiting monomers useful in the invention may include norbornene, norbornadiene, isobutylene, isoprene, vinylbenzocyclobutane, styrenes, alkyl substituted styrene, ethylidene norbornene, dicyclopentadiene and cyclopentene.

In the most preferred embodiment of the process of the invention, a copolymer of ethylene is produced, where with ethylene, a comonomer having at least one alpha-olefin having from 4 to 15 carbon atoms, preferably from 4 to 12 carbon atoms, and most preferably from 4 to 8 carbon atoms, is polymerized in a gas phase process.

In another embodiment of the process of the invention, ethylene or propylene is polymerized with at least two different comonomers, optionally one of which may be a diene, to form a terpolymer.

In one embodiment, the invention is directed to a polymerization process, particularly a gas phase or slurry phase process, for polymerizing propylene alone or with one or more other monomers including ethylene, and/or other olefins having from 4 to 12 carbon atoms. Polypropylene polymers may be produced using the particularly bridged bulky ligand metallocene-type catalysts as described in U.S. Pat. Nos. 5,296,434 and 5,278,264, both of which are herein incorporated by reference.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228, all of which are fully incorporated herein by reference.)

The reactor pressure in a gas phase process may vary from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in a gas phase process may vary from about 30° C. to about 120° C., preferably from about 60° C. to about 115° C., more preferably in the range of from about 70° C. to 110° C., and most preferably in the range of from about 70° C. to about 95° C.

Other gas phase processes contemplated by the process of the invention include those described in U.S. Pat. Nos. 5,627,242, 5,665,818 and 5,677,375, and European publications EP-A-0 794 200, EP-A-0 802 202 and EP-B-634 421 all of which are herein fully incorporated by reference.

In a preferred embodiment, the reactor utilized in the present invention is capable and the process of the invention is producing greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

A slurry polymerization process generally uses pressures in the range of from about 1 to about 50 atmospheres and even greater and temperatures in the range of 0° C. to about 120° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

A preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In an embodiment the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

Examples of solution processes are described in U.S. Pat. Nos. 4,271,060, 5,001,205, 5,236,998 and 5,589,555, which are fully incorporated herein by reference.

A preferred process of the invention is where the process, preferably a slurry or gas phase process is operated in the presence of a bulky ligand metallocene-type catalyst system of the invention and in the absence of or essentially free of any scavengers, such as triethylaluminum, trimethylaluminum, tri-isobutylaluminum and tri-n-hexylaluminum and diethyl aluminum chloride, dibutyl zinc and the like. This preferred process is described in PCT publication WO 96/08520 and U.S. Pat. Nos. 5,712,352 and 5,763,543, which are herein fully incorporated by reference.

Polymer Product of the Invention

The polymers and blends including the polymers produced in the process of the invention utilizing low comonomer incorporating metallocenes can be used in a wide variety of products and end-use applications. The polymers produced by the process of the invention include linear low density polyethylene, elastomers, plastomers, high density polyethylenes, low density polyethylenes, polypropylene and polypropylene copolymers.

The polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc to about 0.930 g/cc.

The melt strength of the polymers produced using the catalyst of the invention are greater than 6 cN, preferably greater than 7 cN, and most preferably 8 cN or higher. For purposes of this patent application and appended claims melt strength is measured with an Instron capillary rheometer in conjunction with the Goettfert Rheotens melt strength apparatus. A polymer melt strand extruded from the capillary die is gripped between two counter-rotating wheels on the apparatus. The take-up speed is increased at a constant acceleration of 24 mm/sec$^2$, which is controlled by the Acceleration Programmer (Model 45917, at a setting of 12). The maximum pulling force (in the unit of cN) achieved before the strand breaks or starts to show draw-resonance is determined as the melt strength. The temperature of the rheometer is set at 190° C. The capillary die has a length of one inch (2.54 cm) and a diameter of 0.06" (0.15 cm). The polymer melt is extruded from the die at a speed of 3 inch/min (7.62 cm/min). The distance between the die exit and the wheel contact point should be 3.94 inches (100 mm).

The polymers produced by the process of the invention typically have a molecular weight distribution, a weight average molecular weight to number average molecular weight ($M_w/M_n$) of greater than 1.5 to about 15, particularly greater than 2 to about 10, more preferably greater than about 2.5 to less than about 8, and most preferably from 3 to 8.

In one preferred embodiment, the polymers of the present invention have a $M_z/M_w$ of greater than or equal to 3, preferably greater than 3. $M_z$ is the z-average molecular weight. In another preferred embodiment, the polymers of the invention have a $M_z/M_w$ of greater than or equal to 3.0 to about 4. In yet another preferred embodiment, the $M_z/M_w$ is in the range greater than 3 to less than 4.

Also, the polymers of the invention typically have a narrow composition distribution as measured by Composition Distribution Breadth Index (CDBI). Further details of determining the CDBI of a copolymer are known to those skilled in the art. See, for example, PCT Patent Application WO 93/03093, published Feb. 18, 1993, which is fully incorporated herein by reference.

The polymers of the invention in one embodiment have CDBI's generally in the range of greater than 50% to 100%, preferably 99%, preferably in the range of 55% to 85%, and more preferably 60% to 80%, even more preferably greater than 60%, still even more preferably greater than 65%. In another embodiment, the polymers have a CDBI less than 50%, more preferably less than 40%, and most preferably less than 30%.

The polymers of the present invention in one embodiment have a melt index (MI) or ($I_2$) as measured by ASTM-D-1238-E in the range from 0.01 dg/min to 1000 dg/min, more preferably from about 0.01 dg/min to about 100 dg/min, even more preferably from about 0.1 dg/min to about 50 dg/min, and most preferably from about 0.1 dg/min to about 10 dg/min.

The polymers of the invention in an embodiment have a melt index ratio ($I_{21}/I_2$) ($I_{21}$ is measured by ASTM-D-1238-F) of from 30 to less than 200, more preferably from about 35 to less than 100, and most preferably from 40 to 95.

The polymers of the invention in a preferred embodiment have a melt index ratio ($I_{21}/I_2$) ($I_{21}$ is measured by ASTM-D-1238-F) of from preferably greater than 30, more preferably greater than 35, even more preferably greater that 40, still even more preferably greater than 50 and most preferably greater than 65.

The polymers of the invention may be blended and/or coextruded with any other polymer. Non-limiting examples of other polymers include linear low density polyethylenes produced via conventional Ziegler-Natta and/or metallocene catalysis, elastomers, plastomers, high pressure low density polyethylene, high density polyethylenes, polypropylenes and the like.

Polymers produced by the process of the invention and blends thereof are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, geomembranes, and pond liners. Molded articles include single and multi-layered constructions in the form of bottles, tanks, large hollow articles, rigid food containers and toys, etc.

The following examples are offered to provide a better understanding of the present invention, including representative advantages thereof.

EXAMPLES

Melt Index (MI) and Flow Index (FI) $I_2$ and $I_{21}$ were measured according to ASTM D-1238, Condition E and F respectively. Melt Index Ratio (MIR) is the ratio of $I_{21}$ over $I_2$. Density was measured according to ASTM D 1505.

Compositional distribution breadth index (CDBI) is defined as the weight percent of the copolymer molecules having a comonomer content within 50% of the median total molar comonomer content. The CDBI of linear polyethylene, which does not contain a comonomer, is defined to be 100%. The CDBI is calculated from data obtained from temperature rising elution fractionation (TREF) or from crystallization analysis fractionation (CRYSTAF) as is known in the art.

For purposes herein, Cp denotes a cyclopentadienyl ligand, Me$_5$Cp denotes a pentamethylcyclopentadienyl ligand, Ind denotes an indenyl ligand, Fl denotes a fluorenyl ligand, and n-BuLi denotes n-butyl lithium.

Standard Schlenk/air sensitive techniques were used for the synthesis of metallocenes, their activation and supporting, and for handling of the supported catalysts. Dry, air-free solvents were used such as those sold commercially by Aldrich, Milwaukee, Wis., (Aldrich) with the proviso that ethereal solvents were free of inhibitor.

1,3-Dichloro-1,1,3,3-tetramethyl disiloxane (ClMe$_2$SiOSiMe$_2$Cl) is available from Aldrich, or from Gelest, Tullytown, Pa. (Me$_5$Cp)$_2$ZrCl$_2$ is available from Strem Chemicals, Newburyport, Mass. Cp$_2$ZrCl$_2$ is available from Aldrich. Ind$_2$ZrCl$_2$, Dimethylsilylene bis(4,5,6,7 tetrahydroindenyl)ZrCl$_2$, Bis(1-methyl, 3-n-butylcyclpentadienyl)ZrCl$_2$, Dimethylsilylene bis(indenyl)ZrCl$_2$, Dimethylsilylene bis(2-methyl indenyl)ZrCl$_2$, and Ethylenebisindenylzirconium dichloride are also available from Aldrich or from Boulder Scientific, Boulder, Colo. The methylalumoxane used was as a 30 wt % in toluene purchased from Albemarle, Baton Rouge, La., and was refrigerated when not in use.

$(Me_5Cp)IndZrCl_2$ was prepared by reacting $(Me_5Cp)ZrCl_3$ with indenyllithium in toluene followed by filtration, washing, and recrystallization from cold methylene chloride/pentane as is known in the art. $(Cp)IndZrCl_2$ was prepared according to the method disclosed in WO 98/28350.

Example 1A

Synthesis of meso-O(Me$_2$SiInd)$_2$ZrCl$_2$

The ligand O(Me$_2$SiIndH)$_2$ was produced by the reaction of ClMe$_2$SiOSiMe$_2$Cl with two equivalents of indenyllithium. This was deprotonated with two equivalents of n-BuLi in tetrahydrofuran (thf) to afford O(Me$_2$SiIndLi)$_2$ as a thf adduct. Various solvents may be used, but if they are not sufficiently solubilizing of the product, precipitation after mono-deprotonation may occur leading to incomplete reaction and unconsumed deprotonating agent. Conditions may be optimized to reduce attack of the siloxane by e.g. the deprotonating agent and side reactions such as polymerization. The meso-O(Me$_2$SiInd)$_2$ZrCl$_2$ was produced in modest yield by reacting O(Me$_2$SiIndLi)$_2$(thf)$_n$ with ZrCl$_4$ in toluene, filtering, washing with toluene, extracting the product into methylene chloride, and recrystallizing.

Example 1B

Alternate Synthesis of meso-O(Me$_2$SiInd)$_2$ZrCl$_2$

In a 5 L round bottom flask under nitrogen, 103.1 g of ClMe$_2$SiOSiMe$_2$Cl (Aldrich) was mixed with 500 mL of inhibitor free tetrahydrofuran followed by cooling to −78° C. A solution of 123.9 g indenyllithium in 1 L of inhibitor free tetrahydrofuran was slowly cannulated into the 5 L flask. The cooling was removed and the mixture allowed to warm to room temperature over night. The reaction was then cooled again to −78 C, 406 mL of 2.5 M n-BuLi in hexanes (Aldrich) was slowly added, cooling removed, and the mixture allowed to warm to room temperature over night. The reaction was transferred into a drybox and 118.2 g ZrCl$_4$ (Cerac, Milwaukee, Wis.) was slowly added and then stirred overnight. NMRs of aliquots generally showed about >4:1, rac:meso in the crude product mixture. The solvent was stripped under vacuum. Toluene, 2.5 L, was added and stirred. After 2 hr the mixture was filtered via Celite and washed with toluene. The precipitates were stirred with 2 L methylene chloride and filtered again through Celite. The filtrate was concentrated and cooled to −35° C. over night. The precipitates were isolated by filtration to yield 15.4 g (6%) of meso-O(Me$_2$SiInd)$_2$ZrCl$_2$.

Example 2

Synthesis of rac-O(Me$_2$SiInd)$_2$ZrCl$_2$ (Ind=indenyl)

The rac isomer was isolated by precipitation from the toluene soluble fraction and the final methylene chloride filtrate from the meso syntheses above in Example 1B. Standard techniques such as concentration, precipitation by pentane, and cooling were employed.

The $^1$H-NMR spectra of the isomers are very distinct. Treatment of the rac isomer with two equivalents of MeLi (methyl lithium) caused the appearance of one new Me (methyl) resonance while similar treatment of the meso lead to two new Me signals.

Figure 3A:
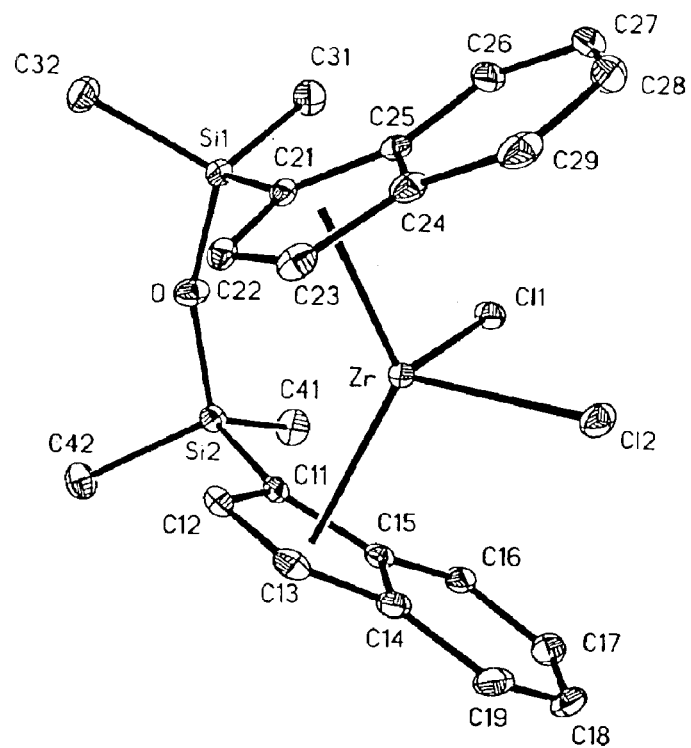
FIG. 3A is a side view of the X-ray structure of meso-O (Me$_2$SiInd)$_2$ZrCl$_2$
Figure 3B:
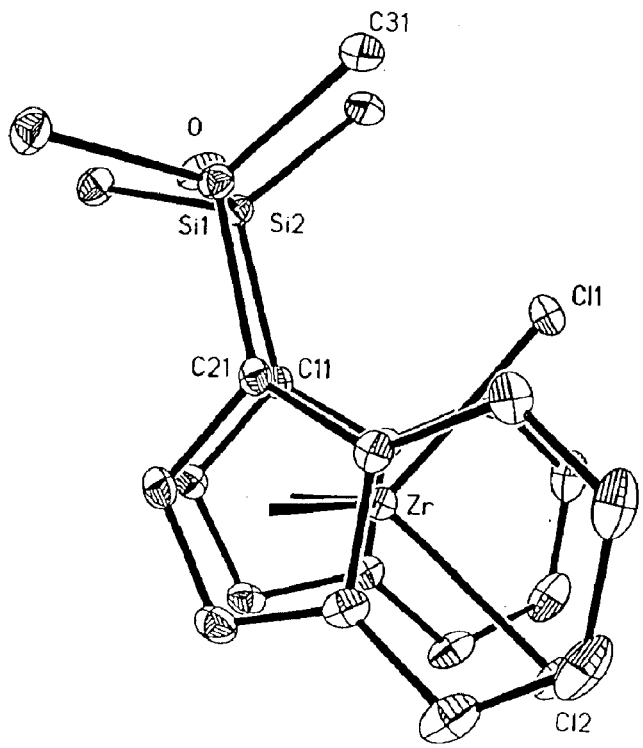
FIG. 3B is a top view of the X-ray structure of meso-O (Me$_2$SiInd)$_2$ZrCl$_2$
Figure 4A:
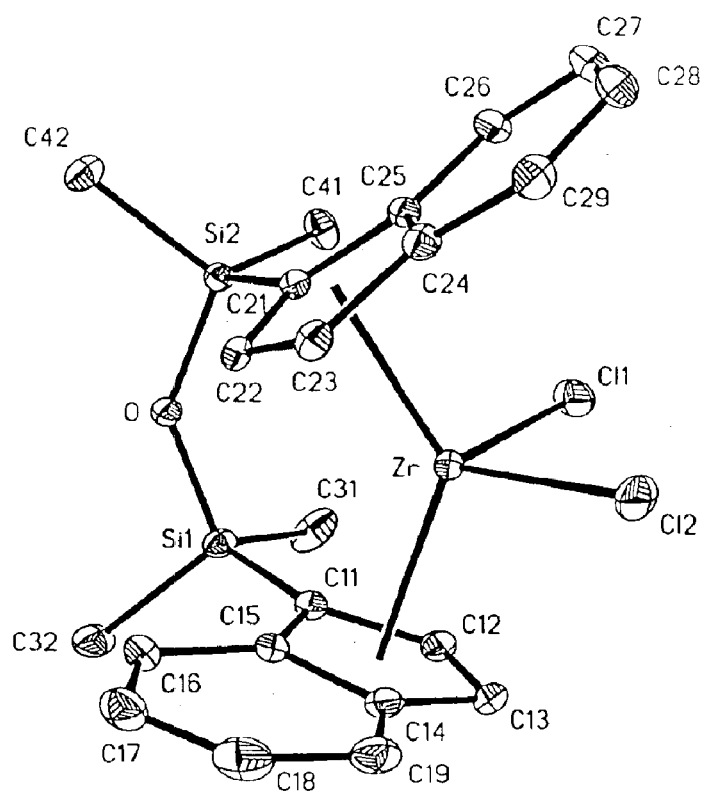
FIG. 4A is a side view of the X-ray structure of rac-O (Me$_2$SiInd)$_2$ZrCl$_2$
Figure 4B:
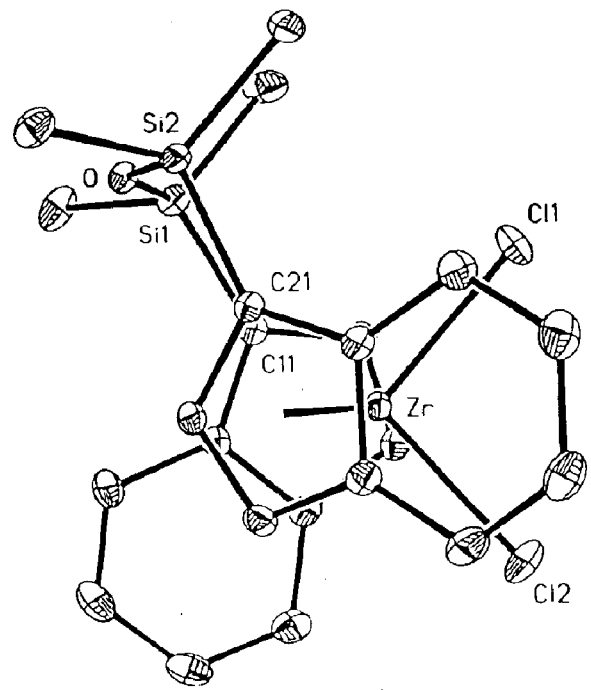
FIG. 4B is a top view of the X-ray structure of rac-O (Me$_2$SiInd)$_2$ZrCl$_2$
Figure 5A:
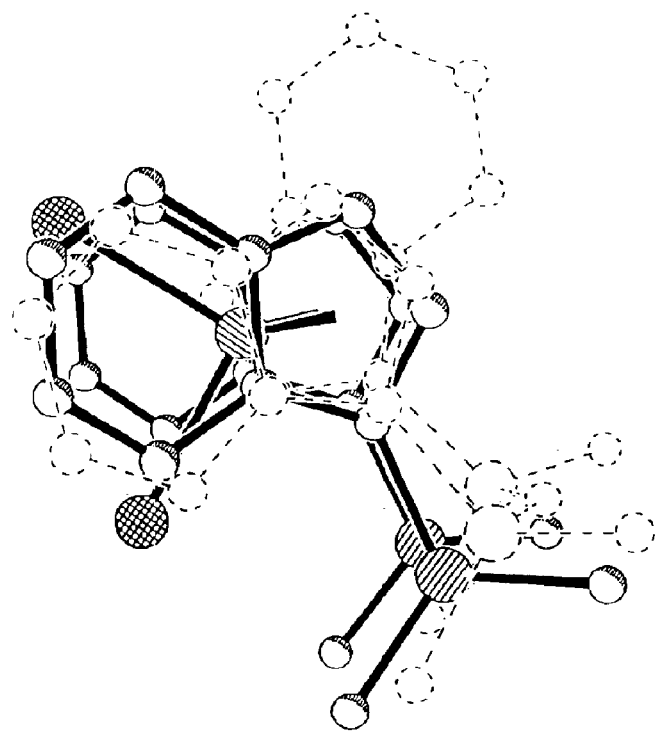
FIG. 5A is a top view of the dashed line X-ray structure of rac-O(Me$_2$SiInd)$_2$ZrCl$_2$, shown imposed over the solid line the X-ray structure of meso-O(Me$_2$SiInd)$_2$ZrCl$_2$.
Figure 5B:
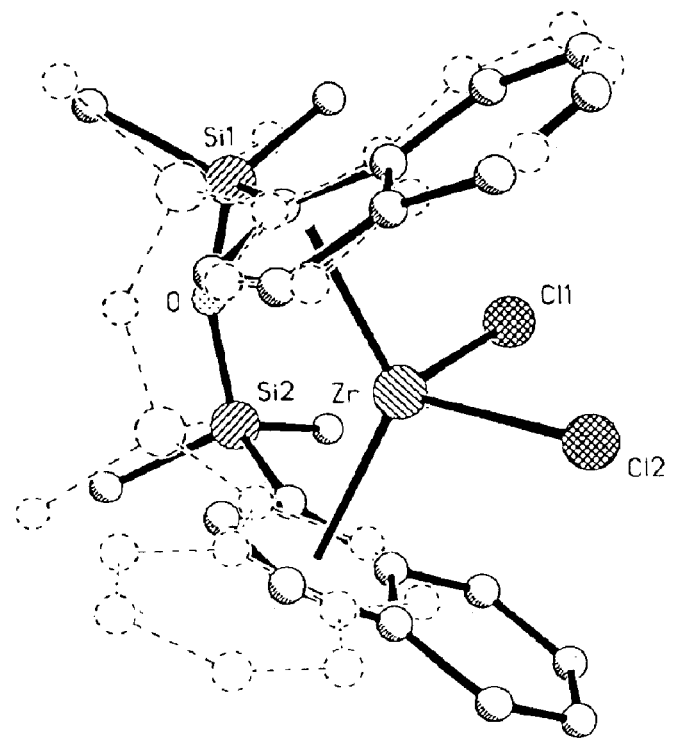
FIG. 5B is a side view of the dashed line X-ray structure of rac-O(Me$_2$SiInd)$_2$ZrCl$_2$, shown imposed over the solid line the X-ray structure of meso-O(Me$_2$SiInd)$_2$ZrCl$_2$.

The X-ray structural analysis of meso-O(Me$_2$SiInd)$_2$ZrCl$_2$ is shown in Tables 3A and 3B with a side view and a top view of the X-ray structure shown in FIGS. 3A and 3B respectively. The X-ray structural analysis of rac-O (Me$_2$SiInd)$_2$ZrCl$_2$ is shown in Tables 4A and 4B with a side view and a top view of the X-ray structure shown in FIGS. 4A and 4B respectively. A top view of the dashed line X-ray structure of rac-O(Me$_2$SiInd)$_2$ZrCl$_2$, imposed over the solid line the X-ray structure of meso-O(Me$_2$SiInd)$_2$ZrCl$_2$ is shown in FIGS. 5A and 5B respectively.

Example 3A

Catalyst Supporting Technique

The catalysts were activated by methylalumoxane (Albemarle 30 wt % MAO in toluene) and supported on silica (Davison 948) such that by material balance the final dry catalyst loading of zirconium was approximately 0.35 wt %, the loading of Al about 12 wt %, and Al/Zr (molar) was about 120. In a typical laboratory preparation the MAO was weighed into a round bottom flask on a balance, toluene added sufficient that the total liquid volume would be about 1.25–1.75 times that of the silica pore volume, then the metallocenes were added and stirred until dissolution. After about 20 minutes the silica was added and the pasty mixture stirred by hand with a spatula for 10 min until well mixed. Next solvent was stripped in vacuo.

Example 3B

Alternate Catalyst Supporting Technique

Alternately, enough toluene could be added to form a liquid slurry, usually more than about 2.3 times the silica pore volume, as is typically done for kilogram scale preparations, resulting in longer drying times. Likewise the solvent could alternately be removed using a nitrogen purge. Kilogram scale preparations were performed in larger vessels, typically two gallon capacity, equipped with mechanical stirring consisting of a stir shaft with downward mixing auger and two upward mixing helical ribbons on the outside. Heat can be used to speed drying.

Example 4

Polymerization Processes

The catalysts described above were then separately tested in a continuous gas phase fluidized bed reactor which comprised either an 8 inch (15.2 cm), 12 inch (30.5 cm), or 18 inch (45.7 cm) diameter reactor body. Typical polymerizations were conducted in a nominal 18 inch, schedule 60 steel reactor having an internal diameter of 16.5 inches (41.9 cm). The fluidized bed, present in each such type reactor, is made up of polymer granules. The gaseous feed streams of ethylene and hydrogen together with liquid comonomer were mixed together in a mixing tee arrangement and introduced below the reactor bed into the recycle gas line. Hexene-1 was used as the comonomer. The individual flow rates of ethylene, hydrogen and comonomer were controlled to maintain fixed composition targets. The ethylene concentration was controlled to maintain a constant ethylene partial pressure. The hydrogen was controlled to maintain constant hydrogen to ethylene mole ratio. The concentration of all the gases was measured by an on-line gas chromatograph to ensure relatively constant composition in the recycle gas stream. The solid supported metallocene, listed in Table 1, was injected directly into the fluidized bed using purified nitrogen at 1.5 lbs/hr (0.68 kg/hr). The reacting bed of growing polymer particles was maintained in a fluidized state by the continuous flow of the make up feed and recycle gas through the reaction zone. A superficial gas velocity of 1 to 3 ft/sec (30.5 cm/sec to 91.4 cm/sec) was used to achieve this. The reactor was operated at a total pressure of 300 psig (2069 kPa), a reactor temperature of 85° C. and a superficial gas velocity of 2.25 ft/sec (68.6 cm/sec) was used to achieve fluidization of the granules. To maintain a constant reactor temperature, the temperature of the recycle gas is continuously adjusted up or down to accommodate any changes in the rate of heat generation due to the polymerization. The fluidized bed was maintained at a constant height by withdrawing a portion of the bed at a rate equal to the rate of formation of particulate product. The product is removed semi-continuously via a series of valves into a fixed volume chamber, which is simultaneously vented back to the reactor. This allows for highly efficient removal of the product, while at the same time recycling a large portion of the unreacted gases back to the reactor. This product is purged to remove entrained hydrocarbons and treated with a small stream of humidified nitrogen to deactivate any trace quantities of residual catalyst. The results appear in Table 1.

It is well known to those skilled in the art that in gas phase and slurry processes that metallocene catalysts tend to give lower productivities when higher density polymers are produced. Indeed, in the same pilot plant gas phase reactor under generally similar conditions catalysts of the complexes CpInd (1), Ind2 (0.7), Me5CpCp (0.3), Me5CpInd (0.3), and (Me5Cp)2 (0.1) give increasingly higher density polymer at decreasing productivity (relative productivity in parenthesis). In contrast, a catalyst of the complex meso-SiOSi gave a relative productivity of about 0.5 despite being very sterically crowded and a much poorer incorporator than all of the other examples except (Me5Cp)2. Similarly rac-SiOSi displayed relative productivity of approximately 0.5. This illustrates the particular utility of long bridged species, particularly with SiOSi linkages, with fused rings as poor comonomer incorporators.

In light of the above, and referring to Table 1, in gas phase ethylene polymerization, $(Me_5Cp)IndZrCl_2$ (Ind=indenyl) shows moderate comonomer incorporation and good activity, $rac-O(Me_2SiInd)_2ZrCl_2$ (Ind=indenyl) shows poor comonomer incorporation and good activity, $meso-O(Me_2SiInd)_2ZrCl_2$ (Ind=indenyl) shows even poorer comonomer incorporation and good activity, and $(Me_5Cp)_2ZrCl_2$ shows the poorest comonomer incorporation and relatively worse activity.

TABLE 1

Figure 2:
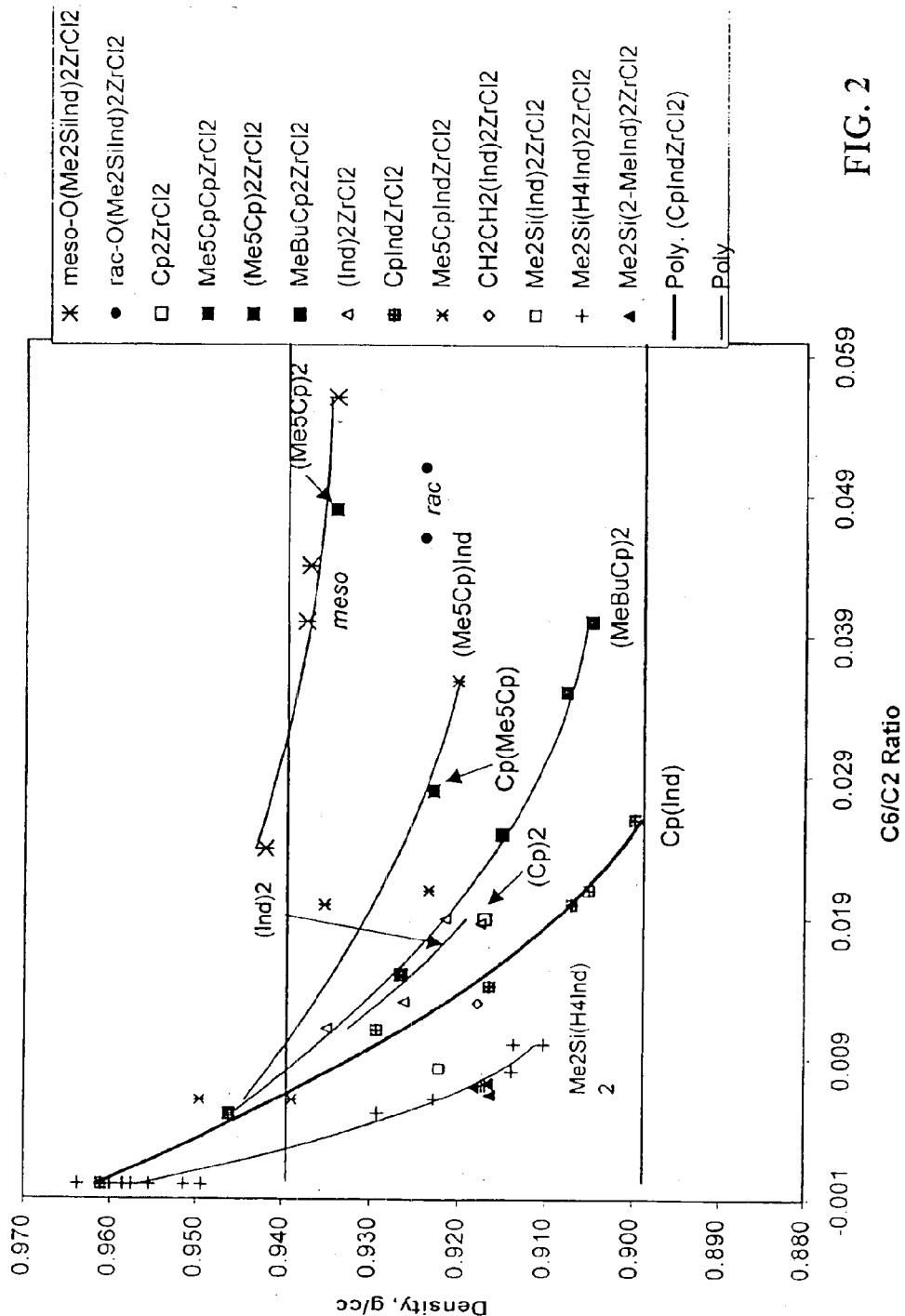
FIG. 2 is a plot of Comonomer (hexane) to Ethylene Ratio vs. Density of Polyethylene Produced for several metallocene catalyst compounds.

Data Points utilized in Comonomer Ratio vs. Density Graph (FIG. 2)

| Catalyst Ligand Set | C6/C2 | Gradient Density | MI | MFR | H2 ppm/% C2 |
|---|---|---|---|---|---|
| (Me₄Cp)₂ | 0.022 | 0.927 | 2.8 | 20.6 | 1.8 |
| (Me₄Cp)₂ | 0.018 | 0.934 | 3.7 | 19.6 | 2.1 |
| (Me₄Cp)₂ | 0.027 | 0.922 | 2.4 | 23 | 1.6 |
| (Me5Cp)₂ | 0.048 | 0.934 | 1.23 | — | 0.7 |
| meso-O(Me2SiInd)₂ | 0.024 | 0.942 | 0.89 | 27.5 | 2.2 |
| meso-O(Me2SiInd)₂ | 0.040 | 0.937 | 1.34 | 35.8 | 2.6 |
| meso-O(Me2SiInd)₂ | 0.044 | 0.937 | 1.4 | 25.8 | 3.0 |
| meso-O(Me2SiInd)₂ | 0.056 | 0.934 | 1.17 | 27.5 | 2.1 |
| rac-O(Me2SiInd)₂ | 0.046 | 0.924 | 1.3 | 30.1 | 0.5 |
| rac-O(Me2SiInd)₂ | 0.051 | 0.924 | 5.23 | 34.4 | 0.7 |
| Cp(Ind) | 0.021 | 0.905 | 1.79 | 19.4 | 5.8 |
| Cp(Ind) | 0.026 | 0.900 | 1.31 | 21.4 | 4.8 |
| Cp(Ind) | 0.020 | 0.907 | 1.1 | 21 | 7.6 |
| Cp(Ind) | 0.000 | 0.961 | 23.8 | 17.2 | 5.7 |
| Cp(Ind) | 0.011 | 0.929 | 23.2 | 19.4 | 10.0 |
| Cp(Ind) | 0.014 | 0.917 | 1.32 | 19.4 | 2.9 |
| Cp2 | 0.019 | 0.917 | 0.48 | 59 | 6.1 |
| (Me5Cp)Ind | 0.021 | 0.924 | 1.43 | 15.7 | 1.1 |
| (Me5Cp)Ind | 0.006 | 0.939 | 0.39 | 19 | 0.7 |
| (Me5Cp)Ind | 0.006 | 0.950 | 24.85 | 18.5 | 4.8 |
| (Me5Cp)Ind | 0.020 | 0.935 | 35.03 | 18.2 | 4.9 |
| (Me5Cp)Ind | 0.036 | 0.920 | 1.18 | 17.45 | 0.7 |
| (Me5Cp)Cp | 0.028 | 0.923 | 1.22 | 34 | 6.5 |
| (Ind)₂ | 0.019 | 0.918 | 3.74 | 16.91 | 2.6 |
| (Ind)₂ | 0.019 | 0.922 | 83.23 | 26.62 | 11.6 |
| (Ind)₂ | 0.011 | 0.935 | 111.52 | 10.21 | 11.2 |
| (Ind)₂ | 0.013 | 0.926 | 3.56 | 17.23 | 1.9 |
| Me2Si(H4Ind)₂ | 0.000 | 0.964 | 7.95 | 0 | 7.3 |
| Me2Si(H4Ind)₂ | 0.000 | 0.960 | 2.86 | 29.8 | 3.7 |
| Me2Si(H4Ind)₂ | 0.000 | 0.959 | 1.51 | 0 | 4.8 |
| Me2Si(H4Ind)₂ | 0.000 | 0.958 | 1.302 | 27.3 | 3.8 |
| Me2Si(H4Ind)₂ | 0.000 | 0.955 | 1.117 | 32.4 | 3.0 |
| Me2Si(H4Ind)₂ | 0.000 | 0.951 | 0.71 | 0 | 6.4 |
| Me2Si(H4Ind)₂ | 0.000 | 0.949 | n/a | ? | 1.4 |
| Me2Si(H4Ind)₂ | 0.005 | 0.929 | 1.852 | 35.2 | 9.4 |
| Me2Si(H4Ind)₂ | 0.006 | 0.923 | 1.64 | 33.4 | 9.7 |
| Me2Si(H4Ind)₂ | 0.007 | 0.917 | 0.34 | 59.3 | 7.4 |
| Me2Si(H4Ind)₂ | 0.007 | 0.917 | 0.67 | 47.5 | 9.0 |
| Me2Si(H4Ind)₂ | 0.008 | 0.914 | 0.44 | 51.5 | 7.5 |
| Me2Si(H4Ind)₂ | 0.010 | 0.914 | 1.29 | 39.4 | 11.3 |
| Me2Si(H4Ind)₂ | 0.010 | 0.910 | 1.24 | 41.7 | 10.4 |
| CH2CH2(Ind)₂ | 0.013 | 0.918 | 1.95 | 45.20 | 11.8 |

TABLE 1-continued

Data Points utilized in Comonomer Ratio vs. Density Graph (FIG. 2)

| Catalyst Ligand Set | C6/C2 | Gradient Density | MI | MFR | H2 ppm/% C2 |
|---|---|---|---|---|---|
| Me2Si(Ind)$_2$ | 0.008 | 0.922 | 0.91 | 85.97 | 43.1 |
| Me2Si(2-MeInd)$_2$ | 0.006 | 0.916 | 1.48 | 57.78 | 40.8 |
| Me2Si(2-MeInd)$_2$ | 0.007 | 0.918 | 0.75 | 78.50 | 34.1 |
| Me2Si(2-MeInd)$_2$ | 0.007 | 0.917 | 0.14 | 107.00 | 20.0 |

TABLE 2

Polynomial Equations Used to Fit Comonomer Response Data (FIG. 2)

| Catalyst | Equation | Set Intercept to |
|---|---|---|
| (Me$_4$Cp)2 ZrC12 | y = 6.8031x2 − 1.6044x + 0.96 | 0.96 |
| Me$_2$Si(H$_4$Ind)2ZrC12 | y = 300.75x2 − 7.5505x + 0.9566 | not set |
| Cp(Ind) ZrC12 | y = 52.58x2 − 3.7679x + 0.9615 | not set |
| (Ind)2 ZrC12 | y = 40.974x2 − 2.9269x + 0.96 | 0.96 |
| (Me5Cp)Ind ZrC12 | y = 14.318x2 − 1.4146x + 0.9523 | not set |
| meso-O(Me2SiInd)2 ZrC12 | y = 7.8436x2 − 0.8913x + 0.96 | 0.96 |

TABLE 3A

Crystal data and structure refinement for meso [O(Me2Si)2(C9H6)2]ZrC12.

| | |
|---|---|
| Identification code | Avs10 |
| Empirical formula | C$_{22}$H$_{24}$Cl$_2$OSi$_2$Zr |
| Formula weight | 522.71 |
| Temperature | 233(2) K |
| Wavelength | 0.71073 Å |
| Crystal System | Monoclinic |
| Space Group | C2/c |
| Unit cell dimensions | a = 18.9662(12) Å alpha = 90° |
| | b = 6.9878(5) Å beta = 98.1400(10)° |
| | c = 34.165(2) Å gamma = 90° |
| Volume, Z | 4482.4(5) Å$^3$, 8 |
| Density (calculated) | 1.549 Mg/m$^3$ |
| Absorption coefficient | 0.847 mm$^{-1}$ |
| F(000) | 2128 |
| Crystal size | 0.20 × 0.05 × 0.05 mm |
| θ range for data collection | 2.17 to 28.26° |
| Limiting indices | −24 ≤ h ≤ 16, −9 ≤ k ≤ 8, −44 ≤ l ≤ 41 |
| Reflections collected | 15172 |
| Independent reflections | 5073 (R$_{int}$ = 0.0271) |
| Completeness to θ = 28.26° | 91.0% |
| Absorption correction | SADABS |
| Max. and min. transmission | 0.9589 and 0.8488 |
| Refinement method | Full-matrix least-squares on F$^2$ |
| Data/restraints/parameters | 5073/0/258 |
| Goodness-of-fit on F$^2$ | 1.036 |
| Final R indices [I > 2σ(I)] | R1 = 0.0307, wR2 = 0.0667 |
| R indices (all data) | R1 = 0.0430, wR2 = 0.0701 |
| Extinction coefficient | 0.00041(5) |
| Largest diff. Peak and hole | 0.519 and −0.455 eÅ |

TABLE 3B

Atomic coordinates [× 10$^4$] and equivalent isotropic displacement parameters [Å$^2$ × 10$^3$] for meso-[O(Me2Si)2(C9H6)2]ZrC12. U(eq) one third of the trace of the orthogonalized U$_{ij}$ tensor.

| | x | y | z | U(eq) |
|---|---|---|---|---|
| Zr | 2285(1) | 5911(1) | 1579(1) | 23(1) |
| C1(1) | 2161(1) | 8332(1) | 1055(1) | 32(1) |
| C1(2) | 2412(1) | 8224(1) | 2114(1) | 46(1) |
| C(11) | 3167(1) | 4394(3) | 1205(1) | 25(1) |
| C(12) | 3048(1) | 3042(3) | 1502(1) | 30(1) |
| C(13) | 3283(1) | 3757(3) | 1881(1) | 34(1) |
| C(14) | 3645(1) | 5523(4) | 1834(1) | 32(1) |
| C(15) | 3572(1) | 5927(3) | 1419(1) | 27(1) |
| C(16) | 3880(1) | 7622(3) | 1290(1) | 35(1) |
| C(17) | 4259(1) | 8782(4) | 1566(1) | 49(1) |
| C(18) | 4340(1) | 8349(4) | 1972(1) | 53(1) |
| C(19) | 4038(1) | 6785(4) | 2111(1) | 45(1) |
| C(21) | 1218(1) | 4417(3) | 1192(1) | 25(1) |
| C(22) | 1482(1) | 3040(3) | 1486(1) | 31(1) |
| C(23) | 1431(1) | 3733(4) | 1866(1) | 35(1) |
| C(24) | 1048(1) | 5491(4) | 1823(1) | 33(1) |
| C(25) | 921(1) | 5935(3) | 1408(1) | 28(1) |
| C(26) | 553(1) | 7650(4) | 1285(1) | 37(1) |
| C(27) | 306(1) | 8786(4) | 1563(1) | 53(1) |
| C(28) | 423(1) | 8309(5) | 1969(1) | 56(1) |
| C(29) | 791(1) | 6730(4) | 2102(1) | 47(1) |
| O | 2043(1) | 3596(3) | 577(1) | 39(1) |
| Si(1) | 1223(1) | 3991(1) | 650(1) | 28(1) |
| Si(2) | 2905(1) | 3925(1) | 663(1) | 28(1) |
| C(31) | 834(1) | 6008(4) | 339(1) | 41(1) |
| C(32) | 708(1) | 1777(4) | 512(1) | 44(1) |
| C(41) | 3174(1) | 5869(4) | 346(1) | 45(1) |
| C(42) | 3339(1) | 1667(4) | 543(1) | 42(1) |

TABLE 4A

Crystal data and structure refinement for rac [O(Me2Si)2(C9H6)2]ZrC12

| | |
|---|---|
| Identification code | als10 |
| Empirical formula | C$_{22}$H$_{24}$Cl$_2$OSi$_2$Zr |
| Formula weight | 522.71 |
| Temperature | 233(2) K |
| Wavelength | 0.71073 Å |
| Crystal System | Monoclinic |
| Space Group | P2$_1$/n |
| Unit cell dimensions | a = 10.6512(6) Å alpha = 90° |
| | b = 13.8744(7) Å beta = 98.6830(10)° |
| | c = 15.5114(8) Å gamma = 90° |
| Volume, Z | 2266.0(2) Å$^3$, 4 |
| Density (calculated) | 1.532 Mg/m$^3$ |
| Absorption coefficient | 0.838 mm$^{-1}$ |
| F(000) | 1064 |
| Crystal size | 0.20 × 0.10 × 0.10 mm |
| θ range for data collection | 1.98 to 28.19° |
| Limiting indices | −14 ≤ h ≤ 14, −12 ≤ k ≤ 18, −20 ≤ l ≤ 19 |
| Reflections collected | 15674 |
| Independent reflections | 5177 (R$_{int}$ = 0.0177) |
| Completeness to θ = 28.19° | 92.8% |
| Absorption correction | SADABS |

TABLE 4A-continued

Crystal data and structure refinement for rac [O(Me2Si)2(C9H6)2]ZrCl2

| | |
|---|---|
| Max. and min. transmission | 0.9209 and 0.8503 |
| Refinement method | Full-matrix least-squares on $F^2$ |
| Data/restraints/parameters | 5177/0/258 |
| Goodness-of-fit on $F^2$ | 1.008 |
| Final R indices [I > 2σ(I)] | R1 = 0.0236, wR2 = 0.0617 |
| R indices (all data) | R1 = 0.0286, wR2 = 0.0640 |
| Extinction coefficient | 0.0005(2) |
| Largest diff. Peak and hole | 0.388 and −0.364 eÅ |

TABLE 4B

Atomic coordinates [ × $10^4$ ] and equivalent isotropic displacement parameters [$Å^2$ × $10^3$] for rac [O(Me2Si)2(C9H6)2]ZrCl2. U(eg) is defined as one third of the trace of the orthogonalized $U_{ij}$ tensor

| | x | y | z | U(eq) |
|---|---|---|---|---|
| Zr | 9288(1) | 3083(1) | 2130(1) | 25(1) |
| Cl(1) | 8703(1) | 4375(1) | 1098(1) | 48(1) |
| Cl(2) | 7549(1) | 1994(1) | 1619(1) | 53(1) |
| C(11) | 9856(2) | 4144(1) | 3433(1) | 29(1) |
| C(12) | 8558(2) | 4340(1) | 3088(1) | 33(1) |
| C(13) | 7799(2) | 3531(1) | 3154(1) | 36(1) |
| C(14) | 8582(2) | 2804(1) | 3619(1) | 34(1) |
| C(15) | 9834(2) | 3192(1) | 3820(1) | 31(1) |
| C(16) | 10775(2) | 2652(2) | 4368(1) | 39(1) |
| C(17) | 10459(2) | 1764(2) | 4655(1) | 52(1) |
| C(18) | 9252(3) | 1361(2) | 4396(2) | 57(1) |
| C(19) | 8319(2) | 1853(2) | 3887(2) | 47(1) |
| C(21) | 11531(2) | 3159(1) | 1824(1) | 27(1) |
| C(22) | 11483(2) | 2447(1) | 2479(1) | 29(1) |
| C(23) | 10740(2) | 1661(1) | 2147(1) | 33(1) |
| C(24) | 10412(2) | 1807(1) | 1224(1) | 32(1) |
| C(25) | 10892(2) | 2728(1) | 1023(1) | 29(1) |
| C(26) | 10682(2) | 3053(1) | 149(1) | 38(1) |
| C(27) | 10060(2) | 2462(2) | −484(1) | 47(1) |
| C(28) | 9598(2) | 1550(2) | −279(1) | 48(1) |
| C(29) | 9754(2) | 1222(1) | 556(1) | 42(1) |
| O | 12336(1) | 4616(1) | 3025(1) | 29(1) |
| Si(1) | 11186(1) | 5038(1) | 3516(1) | 32(1) |
| Si(2) | 12534(1) | 4257(1) | 2046(1) | 27(1) |
| C(31) | 10570(2) | 6170(2) | 2979(2) | 58(1) |
| C(32) | 11834(2) | 5252(2) | 4675(2) | 55(1) |
| C(41) | 12101(2) | 5195(1) | 1204(2) | 44(1) |
| C(42) | 14233(2) | 3915(2) | 2103(1) | 41(1) |

We claim:

1. A process for polymerizing olefin(s) to produce a polyethylene, the process comprising contacting in a gas phase reactor ethylene and 1-hexene with a catalyst system, wherein the catalyst system comprises a low comonomer incorporating metallocene catalyst compound having at least one fused ring cyclopentadienyl based ligand and a second ligand, wherein the at least one fused ring cyclopentadienyl base ligand is directed to the front of the molecule by an angle α which is greater than 30 degrees, wherein the low comonomer incorporating metallocene catalyst compound comprises a bridging group having greater than 2 atoms, characterized in that the density of the polyethylene produced using the metallocene catalyst compound, as a function of 1-hexene to ethylene molar ratio, varies by a function greater than $y=14.318x^2-1.4146x+0.9523$, wherein y is the density function and x is the 1-hexene:ethylene monomer mole ratio.

2. The process of claim 1 wherein α is greater than 45°.

3. The process of claim 1 wherein α is greater than 60°.

4. The process of claim 1 wherein α is greater than 80°.

5. The process of claim 1 wherein the second ligand is a second fused ring cyclopentadienyl based ligand, wherein the angle α of the first ligand is 70° to 90° and wherein angle α of the second ligand is greater than 15°.

6. The process of claim 1 wherein the bridging group is represented by a formula selected from the group consisting of R'$_2$Si—NR'—R'$_2$Si, and R'$_2$Si—O—R'$_2$Si, wherein each R' is independently a hydride radical or a hydrocarbyl radical.

7. The process of claim 1 wherein the second ligand is a fused ring cyclopentadienyl based ligand, wherein the angle α of the first ligand is 70 to 90° and wherein the angle α of the second ligand is greater than 45°.

8. The process of claim 1 wherein the polyethylene is film.

9. The process of claim 1 wherein the process is a gas phase process.

10. The process of claim 1 wherein the low comonomer incorporating metallocene catalyst compound is present in a form selected from the group consisting of racemic, meso, and racemic and meso.

11. A process for polymerizing olefin(s) to produce a polyethylene, the process comprising a contacting in a gas phase reactor ethylene and hexene-1 with a catalyst system, wherein the catalyst system comprises a low comonomer incorporating metallocene catalyst compound having at least one fused ring cyclopentadienyl based ligand and containing a bridge having greater than 2 atoms, and a second ligand, characterized in that the density of the polyethylene produced using the metallocene catalyst compound, as a function of 1-hexene to ethylene molar ratio, varies by a function greater than $y=14.318x^2-1.4146x+0.9523$, wherein y is the density function and x is the 1-hexene:ethylene monomer mole ratio.

12. The process of claim 11 wherein the bridging group comprises two or more Group 13 to Group 16 atoms.

13. The process of claim 11 wherein the bridging group is represented by a formula selected from the group consisting of R'$_2$Si—NR'—R'$_2$Si, and R'$_2$Si—O—R'$_2$Si, wherein each R' is independently a hydride radical or a hydrocarbyl radical.

14. The process of claim 11 wherein the low comonomer incorporating metallocene is selected from the group consisting of O(Me$_2$SiInd)$_2$ZrCl$_2$, O(Me$_2$SiFluorenyl)$_2$ZrCl$_2$, O(Me$_2$SiInd)$_2$HfCl$_2$, O(Me$_2$Si[Me$_3$Cp])$_2$ZrCl$_2$, O(Ph$_2$SiInd)$_2$ZrCl$_2$, RN(Me$_2$SiInd)$_2$ZrCl$_2$, and O(Me$_2$Si[Me$_3$CP])(Me$_2$SiInd)ZrCl$_2$, wherein Ind represents an Indenyl group.

15. The process of claim 11 wherein the low comonomer incorporating metallocene catalyst compound is present in a form selected from the group consisting of racemic, meso, and racemic and meso.

16. The process of claim 11 wherein the polyethylene is film.

17. The process of claim 11 wherein the process is gas phase process.

18. A process for polymerizing olefin(s) to produce a polymer product, the process comprising contacting in a gas phase reactor ethylene and 1-hexene with a catalyst system, wherein the catalyst system comprises a low comonomer incorporating metallocene catalyst compound having at least one fused ring cyclopentadienyl based ligand and a second ligand, and at least one leaving group, bonded to a metal atom and including a bridging group having greater than 2 atoms; characterized in that the density of the polyethylene produced using the metalloncene catalyst compound, as a function of 1-hexene to etylene molar ratio, varies by a function greater than $y=14.318x^2-1.4146x+0.9523$, wherein y is the density function and x is the 1-hexene:ethylene monomer mole ratio.

19. The process of claim 18, wherein the second ligand is a second fused ring cyclopentadienyl based ligand, wherein the angle α of the first ligand is about 70° to about 90° and wherein angle α of the second ligand is greater than 15°.

20. The process of claim 18 wherein the bridging group is represented by a formula selected from the group consisting of $R'_2Si-NR'-R'_2Si$, and $R'_2Si-O-R'_2Si$, wherein each R' is independently a hydride radical or a hydrocarbyl radical.

21. The process of claim 18 wherein the second ligand is a fused ring cyclopentadienyl based ligand, wherein the angle α of the first ligand is about 70 to about 90° and wherein the angle α of the second ligand is greater that 45°.

22. The process of claim 18 wherein the polyethylene is a film.

23. The process of claim 18 wherein the process is a gas phase process.

24. The process of claim 18 wherein the low comonomer incorporating metallocene catalyst compound is present in a form selected from the group consisting of racemic, meso, and racemic and meso.

25. The process of claim 18 wherein the low comonomer incorporating metallocene is selected from the group consisting of $O(Me_2SiInd)_2ZrCl_2$, $O(Me_2SiFluorenyl)_2ZrCl_2$, $O(Me_2SiInd)_2HfCl_2$ $O(Me_2Si[Me_3Cp])_2ZrCl_2$, $O(Ph_2SiInd)_2$ $ZrCl_2$, $RN(Me_2SiInd)_2ZrCl_2$, and $O(Me_2Si[Me_3Cp])(Me_2SiInd)ZrCl_2$, wherein Ind represents Indenyl group.

* * * * *